(12) United States Patent
Bacher et al.

(10) Patent No.: US 8,974,455 B2
(45) Date of Patent: Mar. 10, 2015

(54) MEDICAL COAGULATION INSTRUMENT

(75) Inventors: Uwe Bacher, Tuttlingen (DE); Rainer Hermle, Gosheim (DE)

(73) Assignee: Karl Storz GmbH & Co. KG (DE)

( * ) Notice: Subject to any disclaimer, the term of this patent is extended or adjusted under 35 U.S.C. 154(b) by 447 days.

(21) Appl. No.: 12/816,810

(22) Filed: Jun. 16, 2010

(65) Prior Publication Data

US 2010/0331836 A1 Dec. 30, 2010

(30) Foreign Application Priority Data

Jun. 16, 2009 (DE) .................. 10 2009 025 405

(51) Int. Cl.
*A61B 18/14* (2006.01)
*A61B 18/12* (2006.01)

(52) U.S. Cl.
CPC ....... *A61B 18/1482* (2013.01); *A61B 2018/126* (2013.01); *A61B 2018/1467* (2013.01); *A61B 2218/002* (2013.01); *A61B 2218/007* (2013.01); *A61B 2218/008* (2013.01)
USPC ................................. 606/49; 606/41; 606/50

(58) Field of Classification Search
USPC ..................................................... 606/21–52
See application file for complete search history.

(56) References Cited

U.S. PATENT DOCUMENTS

| 5,718,701 | A | * | 2/1998 | Shai et al. ........................ 606/41 |
| 2001/0020167 | A1 | * | 9/2001 | Woloszko et al. ............... 606/45 |
| 2002/0103485 | A1 | * | 8/2002 | Melnyk et al. .................. 606/45 |
| 2002/0111623 | A1 | * | 8/2002 | Durgin et al. ................... 606/45 |
| 2003/0097126 | A1 | | 5/2003 | Woloszko et al. |
| 2005/0015085 | A1 | | 1/2005 | McClurken et al. |
| 2005/0119650 | A1 | | 6/2005 | Sanders et al. |
| 2008/0086121 | A1 | | 4/2008 | Sensenbrenner et al. |

FOREIGN PATENT DOCUMENTS

| DE | 102005013871 A1 | 10/2005 |
| DE | 102005042312 A1 | 3/2006 |
| DE | 69635311 T2 | 4/2007 |
| WO | 0051510 A1 | 9/2000 |
| WO | 2005039427 A1 | 5/2005 |

OTHER PUBLICATIONS

European Search Report; Application No. EP 10 00 6191; Sep. 9, 2010; 6 pages.

* cited by examiner

*Primary Examiner* — Michael Peffley
*Assistant Examiner* — Khadijeh Vahdat
(74) *Attorney, Agent, or Firm* — St. Onge Steward Johnston & Reens LLC

(57) ABSTRACT

A medical coagulation instrument having a shaft as well as at least one electrode tip that extends beyond the distal end of the shaft. To create a coagulation instrument whose electrodes are of simple structure and ensure an atraumatic and safe handling, at least one electrode tip should be widened or be configured as widening in the distal direction.

13 Claims, 2 Drawing Sheets

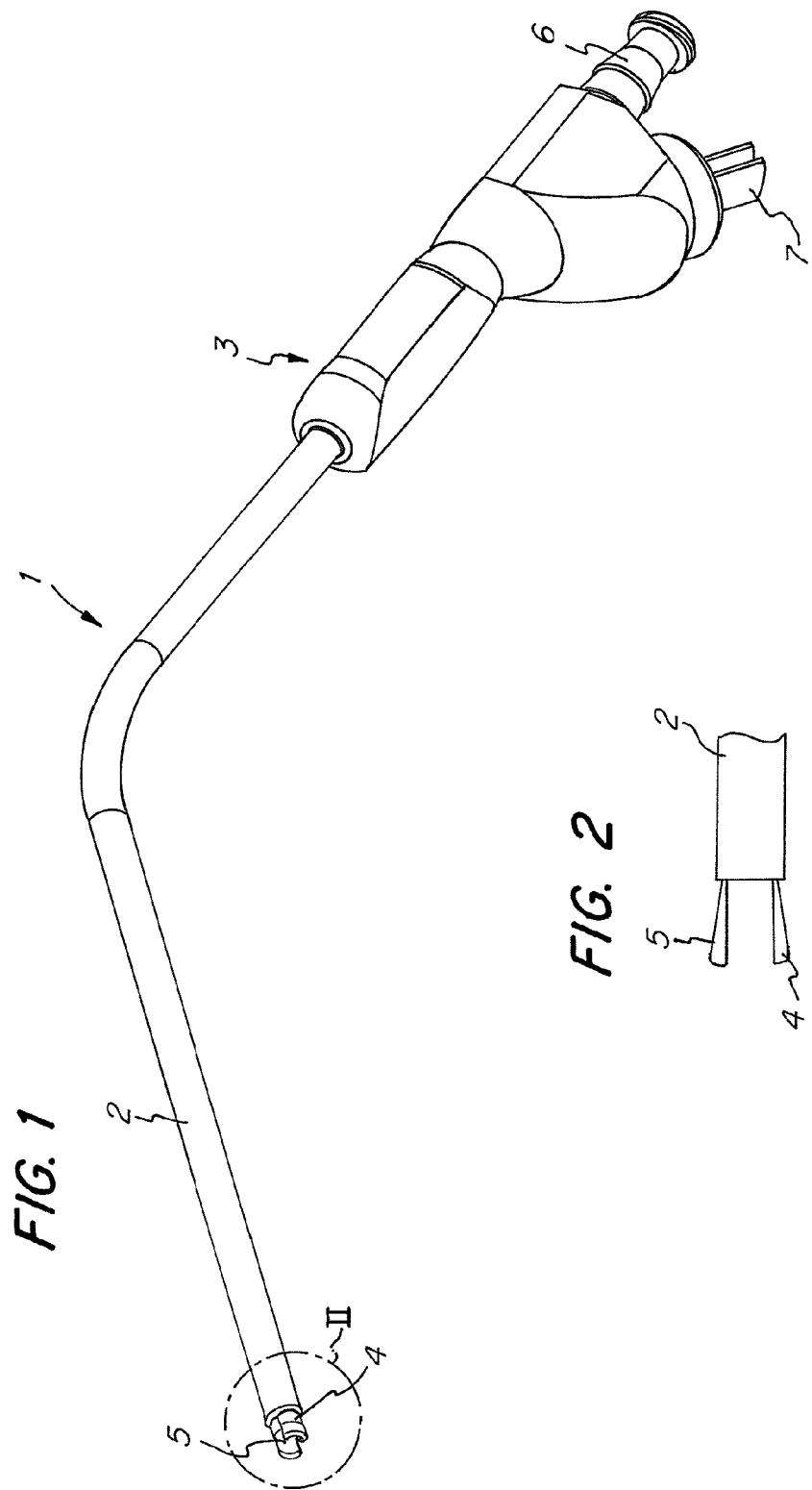

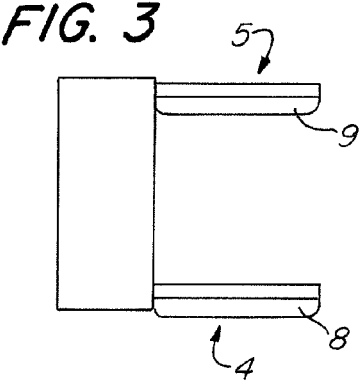
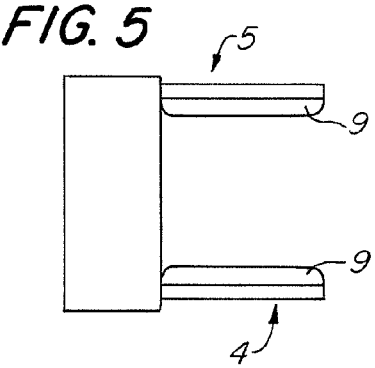
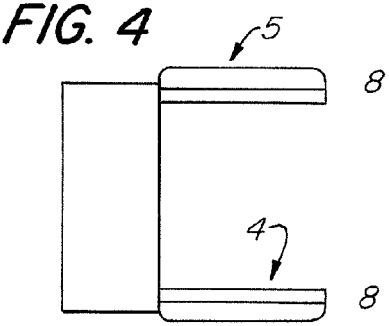
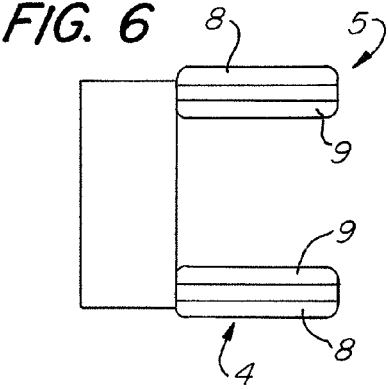

MEDICAL COAGULATION INSTRUMENT

CROSS-REFERENCE TO RELATED APPLICATIONS

The present application claims priority of German patent application No. 10 2009 025 405.6 filed on Jun. 16, 2009.

FIELD OF THE INVENTION

The invention relates to a medical coagulation instrument having a shaft as well as at least one electrode tip extending beyond the distal end of the shaft.

BACKGROUND OF THE INVENTION

Medical coagulation instruments of this type are used in particular to close vessels during operations by means of the at least one electrode tip impinged with current.

Among medical coagulation instruments it is necessary to distinguish between so-called monopolar coagulation instruments and bipolar coagulation instruments. In so-called monopolar coagulation the coagulation instrument comprises an electrode tip that is impinged with current and by means of which the current, with heat generated, enters the tissue on the small contact surface of the electrode tip with the patient. The current is diverted by a neutral electrode with which the patient is in contact on a large surface. The large-surface contact of the patient with the neutral electrode prevents heat development at the current exit point.

In bipolar coagulation the coagulation instrument comprises two electrode tips that are electrically insulated from one another and which both are impinged with current so that energy, with local heat development, passes directly from one electrode tip to the other electrode tip.

A generic medical coagulation instrument configured as a bipolar coagulation instrument is known, for instance, from US 2008/0086121 A1.

A disadvantage of coagulation instruments known in the art is that injuries to patients can result from the insertion of the instrument into the operating area through the at least one electrode extending beyond the distal end of the instrument shaft. In addition, this at least one electrode tip presents only a small distal coagulation surface and is unstable because of its structural configuration.

Consequently it is the object of the invention to configure a bipolar coagulation instrument of the aforementioned type in such a way that its electrodes ensure both simple construction and atraumatic and safe handling.

SUMMARY OF THE INVENTION

This object is achieved in such a way, according to the invention, that the at least one electrode tip is configured as widening in a distal direction. This widening can be either constant or in stages in the axial direction of the coagulation instrument pointing distally. With a step-wise widening, however, attention is required to ensure that said widening is achieved in a position and manner that are atraumatic when applied in an operation.

As a result of the inventive configuration of the electrode tips as widening in the distal direction, it is possible to increase the stability and solidity of the electrodes and simultaneously to reduce the risk of injury to the patient because of the distal widening of the electrodes.

In configuring the medical coagulation instrument as a bipolar coagulation instrument, it is proposed with the invention that two electrode tips that extend beyond the distal end of the shaft and are electrically insulated against one another should be positioned on the distal end of the shaft and should both be configured as widening in the distal direction.

According to a practical embodiment of the invention it is proposed that the electrodes should be configured as thickening in the distal direction in order to increase the solidity of the electrodes by the more massive configuration of the electrode tips.

According to one embodiment of the invention it is proposed that the electrodes should be configured as widening conically in the distal direction. Conical configuration of the electrode tips constitutes an embodiment of the electrodes that is especially easy to manufacture and safe to handle, and which combines increased solidity and simultaneous operational safety.

According to an alternative embodiment of the invention it is proposed that the electrodes should be configured as widening in fan-like manner in the distal direction. Fan-shaped widening of the electrode tips can also lead to increased intrinsic solidity of the electrode tips along with reduction of the risk of injury.

It is further proposed with the invention that to improve the atraumatic operation of the coagulation instrument, the free ends of the electrodes should be configured as rounded.

In addition it is proposed with a preferred embodiment of the invention that to simplify production of the coagulation instrument, a small plate should be applied on the outside on an electrode tip, and in particular it should be welded in place. In this manner the invention includes all manners of joining the small plates to the respective electrode tip and also all combinations of various ways of joining the two small plates.

This small plate preferably and in particular should have the width of the electrode tip so that the entire structure of the electrode tip and the small plate applied to it should form almost a thickened electrode tip.

The distal end of the small plate here can extend as far as the distal end surface of the electrode or of the electrode tip.

The small plate is in particular a pipe segment, but more particularly in the shape and curvature of the electrode tip.

The small plate can have the thickness of the electrode tip or else a lesser or greater thickness.

According to the invention the thickness of the small plate can be constant. However, the thickness of the small plate can also change in the axial direction of the coagulation instrument, in particular widening in the distal direction, or else it can in particular be conical. Besides conical form, the change in thickness of the small plate can also take any other form, such as convex or concave, constant or non-constant.

In the same manner the thickness can also change during the tangential course of the electrode tip. For instance, the thickness can decrease in the direction toward the tangential external portions of the small plate.

To reduce still further the risk of injury from the tangential outer portions of the electrode tip, the small plate could also be widened on its tangential outer portions.

Like the thickness of the electrode tips, the thickness of the small plate can also vary according to the invention. For instance, the thickness of the small plate can increase conically over its axial course, in particular in the distal direction.

The thickness of the small plate can also vary over the tangential course of the small plate. For instance, the thickness in the direction toward the tangential outside portions of the small plate can decrease or else can increase.

In an additional embodiment a small plate can be affixed on the inside of the electrode tip, and in particular can be welded to the electrode tip, in addition to or instead of the small plate on the outside of the electrode tip at the distal end portion of the free end of the electrode.

This inside small plate preferably has the shape and width of the electrode tip.

The inside small plate here is, in particular, a pipe segment.

The inside small plate here can have the thickness of the electrode tip or else a lesser or greater thickness.

According to the invention the thickness of the inside small plate can also vary. For example, the thickness strength of the inside small plate can increase conically along its axial course, in particular in the distal direction.

The thickness strength of the inside small plate can also vary along the tangential course of the small plate. For example, the thickness can decrease in the direction toward the tangential outer portions of the inside small plate.

The outer and/or inside small plate can be affixed not just to one of the two electrodes, but also to both, and in particular can be welded in any form, thus for instance the inside small plate on one electrode and the outside small plate on the other, the inside or outside small plate on both electrodes, or only the inside or outside small plate on one electrode and both small plates on the other. The respective small plates here can each independently have any of the described thickness or thickness changes.

Additional properties and advantages of the invention can be seen from the appended illustrations, in which an embodiment of an inventive medical coagulation instrument is presented by way of example, without restricting the invention to this embodiment.

BRIEF DESCRIPTION OF THE DRAWINGS

FIG. 1 presents a perspective side view of an inventive medical coagulation instrument.

FIG. 2 presents an enlarged depiction of detail II according to FIG. 1 in overhead view.

FIG. 3 presents an enlarged depiction of detail II according to FIG. 1 of a preferred embodiment of the invention in overhead view.

FIG. 4 presents an enlarged depiction of detail II according to FIG. 1 of a second preferred embodiment of the invention in overhead view.

FIG. 5 presents an enlarged depiction of detail II according to FIG. 1 of a third preferred embodiment of the invention in overhead view.

FIG. 6 presents an enlarged depiction of detail II according to FIG. 1 of a fourth preferred embodiment of the invention in overhead view.

DETAILED DESCRIPTION OF THE INVENTION

FIG. 1 shows a medical coagulation instrument 1 that is configured as a bipolar coagulation instrument 1 and is also configured as a suction instrument in addition to its configuration as a coagulation instrument.

This illustrated medical bipolar coagulation instrument 1 consists essentially of a hollow shaft 2 configured as a suction/irrigation channel, a handle 3 positioned on the proximal end of the shaft 2, and two electrode tips 4 and 5 that extend beyond the hollow shaft 2 on the distal end.

To configure the hollow shaft 2 as a suction and/or irrigation channel, the handle 3 comprises on its proximal end a suction and/or irrigation connection 6 for coupling with an external suction and/or irrigation line. The electrode tips 4 and 5 are impinged by means of a current connection 7 positioned on the handle 3.

As can be seen in particular from the detail view of FIG. 2, the finger-type protruding electrode tips 4 and 5 are positioned opposite to one another and are electrically insulated from one another on the distal end of the shaft 2 in such a way that they extend beyond the distal end of the shaft 2.

To give the electrode tips 4 and 5 a higher degree of solidity, the electrode tips 4 and 5 are configured to widen in the distal direction. In the presented embodiment the electrode tips 4 and 5 are configured as widening conically in the distal direction in such a way that the electrode tips 4 and 5 are clearly configured as thicker on the free distal end than at the proximal transition to the shaft 2.

Alternatively to the illustrated conical widening of the electrode tips 4 and 5 toward the distal end, it is also possible to achieve this distal-end widening of the electrode tips 4 and 5 by a fan-shaped widening of the free distal ends of the electrode tips 4 and 5.

In addition to the increase in solidity of the electrode tips 4 and 5, the widening of the free distal ends of the electrode tips 4 and 5 causes an enlargement of the coagulation surfaces, that is, of the surfaces by which the current by heat development enters the patient's tissue.

An additional decisive advantage of the widening of the distal-end free ends of the electrode tips 4 and 5 consists in the fact that the risk of injury to the patient during insertion of the coagulation instrument 1 into the operating area is clearly reduced if the free ends of the electrode tips 4 and 5 are no longer thin and narrow but rather widened and thickened in configuration.

To further improve the possibility of atraumatic use of the coagulation instruments 1 by the widening outward of the electrode tips 4 and 5, the free ends of the electrode tips 4 and 5 shown in FIG. 2 have in addition a rounded-off configuration.

FIG. 3 shows a preferred embodiment of the invention in enlarged view, that is, corresponding to detail II of FIG. 1 in overhead view.

Here the electrode tips 4 and 5 widen in the distal direction, to some extent in stages. In this arrangement, the small plates 8, 9 are affixed to the electrode tips 4 and 5, in particular by welding. All means of joining and combining the small plates 8 and 9 to the respective electrode tips 4 or 5 are also possible.

In this preferred embodiment a small plate 8 is affixed on the outside of electrode tip 4. The small plate 8 can have a constant thickness as shown here.

It is also possible, alternatively, for the thickness of the small plate 8 to change in the axial direction of the coagulation instrument 1, in particular by widening in the distal direction, in particular conically. The thickness of the small plate 8 can likewise be reduced in the distal direction, in particular conically. Aside from conically, the change in thickness of the small plate 8 can also be configured in any other manner, for instance as convex or concave, constant or non-constant. It is particularly preferred for the small plate 8 to be reduced on its edges, in particular the distal edges, in particular by rounding.

This small plate 8 preferably has the shape and in particular the width of the electrode tip 4, so that the total structure of the electrode tip 4 with the small plate 8 affixed to it should form a thickened electrode tip 4. It is important here that the small plate 8 should extend essentially as far as the distal end surface of the electrode or of the electrode tip 4.

Although it is illustrated only in section in FIG. 3, the small plate is preferably a pipe segment, but in particular with the shape and curvature of the electrode tip 4.

As shown in FIG. 3, a small plate 9 is affixed to the electrode tip 5. The small plate 9, like small plate 8, can have a constant thickness. Alternatively, the small plate 9 could have a variable thickness as described for small plate 8. Here all combinations of variable thickness are possible for the small plates 8 and 9.

The shape and in particular the width of the small plate 9 can be the same as for small plate 8, such that all combinations of these various types of shape or of width are possible for the small plates 8 and 9.

FIG. 4 shows a second preferred embodiment of the invention in enlarged view, that is, corresponding to detail II of FIG. 1 in overhead view.

As in FIG. 3, the electrode tips 4 and 5 widen here in the distal direction, to some extent in stages. Here the small plates 8 are affixed to the electrode tips 4 and 5, in particular by welding. It is also possible to use any manner of joining and combining the small plates 8 to the respective electrode tip 4 or 5.

In this second preferred embodiment, a small plate 8 is affixed on the outside on the electrode tip 4. The small plate 8 can have a constant thickness, as described here.

Alternatively, however, the thickness of small plate 8 could also vary in the axial direction of the coagulation instrument 1, in particular widening in the distal direction, in particular conically. The thickness of the small plate 8 can likewise decrease in the distal direction, in particular conically. Aside from conical shape, the variation in thickness of the small plate 8 can also be achieved in any other manner, for instance convex or concave, constant or non-constant. It is especially preferred that the small plate should be reduced on its edges, in particular the distal edge, and in particular by rounding.

This small plate 8 preferably has the shape and in particular the width of the electrode tip 4, so that the total structure of the electrode tip 4 with its applied small plate 8 forms a thickened electrode tip 4. It is important here that the small plate 8 should extend essentially as far as the distal end surface of the electrode and/or of the electrode tip 4.

Although shown only in section in FIG. 4, the small plate is preferably a pipe segment, but in particular with the shape and curvature of the electrode tip 4.

A small plate 8 is likewise affixed externally on the electrode tip 5 according to FIG. 4.

This small plate 8 can have a constant thickness or else, as described for small plate 8, can comprise on the electrode tip 4 a variable thickness. Here all combinations of varying thickness s are possible for both small plates 8.

The shape and in particular the width of this small plate 8 can be as described for the small plate 8 on the electrode tip 4, so that all combinations of these various types of shape and/or of width are possible for both small plates 8.

FIG. 5 presents a third preferred embodiment of the invention in enlarged view, that is, corresponding to detail II of FIG. 1 in overhead view.

As in FIGS. 3 and 4, here the electrode tips 4 and 5 widen in the distal direction, to some extent in stages. In addition, small plates 9 are affixed to the electrode tips 4 and 5, in particular by welding. All means of joining and combining the small plates 9 to the respective electrode tip 4 or 5 can be considered.

With this third preferred embodiment, a small plate 9 is affixed to the electrode tip 4 on the inside. As shown here, the small plate 9 can have a constant thickness.

Alternatively, the thickness of the small plate 9 could also vary in the axial direction of the coagulation instrument 1, or in particular could widen in the distal direction, in particular conically. Likewise the thickness of the small plate 9 can also decrease distally, in particular conically. In addition to conical variation, the thickness of the small plate 9 can also take any other form, for instance convex or concave, constant or nonconstant. It is especially preferable that the small plate 9 should be reduced on its edges, in particular the distal edge, in particular by rounding.

This small plate 9 preferably has the shape and in particular the width of the electrode tip 4, so that the entire structure of the electrode tip 4 with its affixed small plate 9 should form a thickened electrode tip 4. It is important here that the small plate 9 should extend essentially as far as the distal end surface of the electrode or of the electrode tip 4.

Although shown only in section in FIG. 5, the small plate is preferable a pipe segment, but in particular with the shape and curvature of the electrode tip 4.

A small plate 9 is likewise affixed on the inside to the electrode tip 5 as in FIG. 5.

This small plate 9 can have a constant thickness or else, as described for small plate 9 on the electrode tip 4, can have a variable thickness. Here all combinations of varying thicknesses are possible for both small plates 9.

The shape and in particular the width of this small plate 9 can be as described for small plate 9 on the electrode tip 4, such that all combinations of these various types of shape or of width are possible for both small plates 9.

FIG. 6 shows a fourth preferred embodiment of the invention in enlarged view, that is, corresponding to detail II of FIG. 1 in overhead view.

Here, as in FIGS. 3 and 4, the electrode tips 4 and 5 widen in the distal direction and to some extent in stages. Thus small plates 8 and 9 are affixed onto the electrode tips 4 and 5, respectively, in particular by welding. It is also possible to use any types or combinations in joining the small plates 8 and 9 onto the respective electrode tip 4 or 5.

In this fourth preferred embodiment a small plate 8 on the inside and a small plate 9 on the outside are affixed to the electrode tip 4. The small plate 8 like small plate 9 can have a constant thickness as shown here.

The thickness of the plate 8 or 9 could vary alternatively but in each case also in the axial direction of the coagulation instrument 1, in particular widening in the distal direction, in particular conically. The thickness of the small plate 8 or 9 can likewise decrease in the distal direction, in particular conically. Besides changing conically, the change in thickness of the small plate 8 or 9 can be of any other type, for example convex or concave, constant or non-constant. It is especially preferred that the small plates 8 or 9 should be reduced on their edges, particularly on the distal edge, in particular by rounding. Thus the thickness s and reduction/rounding of both small plates 8 and 9 can operate differently and/or for one of the two small plates 8 and 9 the thickness could change and for the other it could not, so that all corresponding combinations are conceivable.

The small plate 8 or the small plate 9 preferably have the shape and in particular the width of the electrode tip 4, so that the entire structure of the electrode tip 4 with its affixed small plates 8 and 9 forms a thickened electrode tip 4. It is important here that the small plate 8 and the small plate 9 extend essentially as far as the distal end surface of the electrode or of the electrode tip 4.

Although shown only in section in FIG. 6, the small plates 8 and 9 are preferably pipe segments, but in particular of the shape and curvature of the electrode tip 4.

According to FIG. 6 a small plate 8 is affixed on the electrode tip 5 on the outside and a small plate 9 on the outside.

These small plates 8 or 9 can each have a constant thickness or else a varying thickness as described for the small plates 8 or 9 on the electrode tip 4. All combinations of varying thickness are possible here for the two small plates 8 or 9.

The shape and in particular the width of these small plates 8 or 9 can be as described for the small plates 8 or 9 on the electrode tip 4, such that all combinations of these various types of shape or width are possible for both small plates 8 or 9.

The medical coagulation instrument configured according to the invention or to the described embodiments is distinguished in that, on the basis of the distal widening of the free ends of the electrode tips 4 and 5, an atraumatic handling of the coagulation instrument is ensured along with simultaneously clearly improved solidity of the electrode tips 4 and 5.

Alternatively to the depiction in FIGS. 1, 2, 3, 4, 5, and 6, it is also possible of course to employ this distal widening of the electrode tips 4 and 5 with other bipolar coagulation instruments or else with monopolar coagulation instruments equipped with only one electrode tip 4.

What is claimed is:

1. A medical coagulation instrument comprising:
   a shaft;
   two electrode tips extending beyond a distal end of the shaft, at least one of said two electrode tips widening in the distal direction; and
   at least one small plate affixed to one of an outer surface, an inner surface, or both an outer and an inner surface of at least one of said two electrode tips, wherein the at least one small plate is electrically conductive;
   said two electrode tips being oriented essentially parallel to one another, the inner surface of each of said two electrode tips facing towards each other and the outer surface of each of said two electrode tips facing away from one another;
   wherein the at least one small plate has a thickness, said thickness of the at least one small plate increases in the distal direction.

2. The medical coagulation instrument according to claim 1, wherein each of said two electrode tips extend beyond the distal end of the shaft are electrically insulated with respect to one another, and widen in the distal direction.

3. The medical coagulation instrument according to claim 1, wherein the two electrode tips are configured as thickening in the distal direction.

4. The medical coagulation instrument according to claim 1, wherein the two electrode tips are configured as widening conically in the distal direction.

5. The medical coagulation instrument according to claim 1, wherein the two electrode tips are configured as widening in fan shape in the distal direction.

6. The medical coagulation instrument according to claim 1, wherein the two electrode tips are configured as widening in stages in the distal direction.

7. The medical coagulation instrument according to claim 6, wherein the two electrode tips comprise sections of constant thickness in the distal direction.

8. The medical coagulation instrument according to claim 1, wherein the at least one small plate has a wideness, said wideness of the at least one small plate increases in the outward direction.

9. The medical coagulation instrument according to claim 1, wherein the thickness of said at least one small plate is essentially equal to a thickness at least one of said two electrode tips.

10. The medical coagulation instrument according to claim 1, wherein a distal end of at least one of said two electrode tips is configured as rounded.

11. The medical coagulation instrument according to claim 1 wherein said at least one small plate is at least two small plates and each of said two electrode tips has one of said two small plates affixed thereto.

12. The medical coagulation instrument according to claim 11, wherein each of the at least one small plate has a wideness, said wideness of the at least one small plate varies, and in particular increases in the outward direction.

13. The medical coagulation instrument according to claim 11, wherein the thickness of each of the at least one small plate is essentially equal to the thickness of at least one of said two electrode tips.

\* \* \* \* \*